United States Patent [19]

Hara et al.

[11] 4,239,843
[45] Dec. 16, 1980

[54] METHOD OF STABILIZING ORGANIC SUBSTRATES AGAINST THE ACTION OF LIGHT

[75] Inventors: Hiroshi Hara, Asaka; Yoshiaki Suzuki, Minami-ashigara, both of Japan

[73] Assignee: Fuji Photo Film Co., Ltd., Minami-ashigara, Japan

[21] Appl. No.: 955,839

[22] Filed: Oct. 30, 1978

[30] Foreign Application Priority Data

Oct. 28, 1977 [JP] Japan .............................. 52-129348

[51] Int. Cl.$^3$ .............................................. G03C 7/00
[52] U.S. Cl. ..................................... 430/17; 430/213; 430/220; 430/372; 430/544; 430/551; 430/552; 430/554; 430/556; 430/558; 430/559; 430/561; 430/933; 260/45.75 R; 260/429 R; 260/438.1; 260/439 R; 8/636; 8/648; 8/664
[58] Field of Search ................... 96/56, 67, 109, 110, 96/84 R, 119, 66.4, 114.5, 74, 99, 100; 252/300 R; 260/429 R, 429 C, 429 J, 438.1, 439 R

[56] References Cited

U.S. PATENT DOCUMENTS

| | | | |
|---|---|---|---|
| 2,208,253 | 7/1940 | Flenner et al. | 260/429 J |
| 2,933,474 | 4/1960 | Handy et al. | 260/429 J |
| 3,298,999 | 1/1967 | Kiriyama et al. | 260/429 R |
| 3,424,815 | 1/1968 | Cannell et a. | 260/429 R |
| 3,458,548 | 7/1969 | Carlson | 260/439 R |
| 3,588,216 | 6/1971 | Bloom | 260/439 R |
| 3,649,247 | 3/1972 | Carlson | 96/56 |
| 3,762,922 | 10/1973 | Lugosg et al. | 96/56 |
| 3,875,199 | 4/1975 | Bloom | 260/429 R |
| 3,885,966 | 5/1975 | Gracia et al. | 96/94 R |
| 4,076,531 | 2/1978 | Crowell | 96/94 R |

OTHER PUBLICATIONS

Photographic Gelatin, Croome et al., Focal Press. N.Y. ©1965, pp. 76-83.
Stabilization of Photographic Silver Halide Emulsions-Birr Focal Press ©1974 pp. 115-117.
Photographic Emulsions, James, NDC, Park Ridge, N.J. ©1973 pp.24-27.

*Primary Examiner*—Travis Brown
*Attorney, Agent, or Firm*—Sughrue, Rothwell, Mion, Zinn and Macpeak

[57] ABSTRACT

The stability of organic substrates having an absorption maximum between 300 and 800 nm in wavelength can be improved by at least one compound represented by the formula (I);

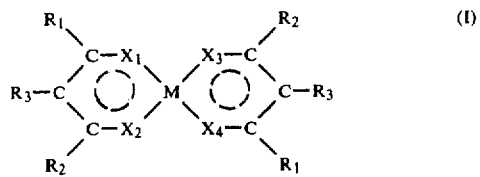

wherein M represents Cu, Co, Ni, Pd or Pt; $X_1$, $X_2$, $X_3$ and $X_4$ each represents an oxygen or sulfur atom, $R_1$ and $R_2$ each represents an alkyl, an aryl, a cycloalkyl, an oxocyclalkyl or a heterocyclic group attached to the carbon atom on the chelate ring directly or through a divalent connecting group, $R_3$ represents a hydrogen atom, an alkyl, an aryl, a cycloalkyl, an oxocycloalkyl or a heterocyclic group attached to the carbon atom on the chelate ring directly or through a connecting group whereby $R_1$, $R_2$ and $R_3$ may be the same or different and $R_1$ and $R_3$ or $R_2$ and $R_3$ may combine with each other to form a 5-, 6- or 7- member ring structure.

12 Claims, No Drawings

_4,239,843_

METHOD OF STABILIZING ORGANIC SUBSTRATES AGAINST THE ACTION OF LIGHT

BACKGROUND OF THE INVENTION

This invention relates to improving the light fastness of organic substrates and more particularly to improving the light fastness of organic compounds useful as dyestuffs.

It is commonly accepted that organic substrates such as, for example, organic dyes tend to fade upon exposure to light. Extensive studies are constantly being carried out in various technical fields such as for printing inks, textile dyeing as well as color photography, in an effort to improve the light fastness of such organic dyes.

The present invention is advantageously used to improve the light fastness of these organic substances.

In the following descriptions, the term "organic substrate" or "organic substrate material" is used to define an organic material appearing colored or colorless to the human eye under the illumination of sunlight, including not only those materials having absorption maxima in the visible spectrum, but also those absorption maxima which lie in the infrared region or in the ultraviolet region such as optical whitening agents. In other words, the organic substrate materials which are the subject of the present invention are materials having their absorption maxima at a wavelength of from 300 to 800 nm. The present invention is particularly directed to improving the light fastness of organic substrate materials occurring in photographic materials, e.g., color films, prints, etc., in colored polymers useful as agricultural vinyl cover sheets, umbrellas, tents, etc.; of fluorescent whitening agents; and dyed textiles, etc.

In this specification, the term "dye" or "dyestuff" refers to an organic material which appears colored to the human eye under the illumination of sunlight. The term "light" conceptually includes electromagnetic radiation with wavelengths of from about 300 nm to about 800 nm, including ultraviolet light below 400 nm, visible light of from about 400 nm to about 700 nm and infrared rays of from about 700 to 800 nm.

It is well known that organic substrates such as, dyes or coloring agents tend to be faded by the action of light. A number of reports discussing methods of suppressing such tendency, or of improving the light fastness of such materials are known. For example, U.S. Pat. No. 3,432,300 discloses that the light fastness of organic compounds such as indophenol, indoaniline, azo and azomethine dyes to visible and UV light can be improved using phenol derivatives containing condensed heterocyclic structures. As "The Theory of Photographic Process" (3rd edition-1967) authored by Mees et al explains in Chapter 17, azomethine or indoaniline dyes are generally produced in silver halide color photographic materials upon the reaction of the oxidation product of an aromatic primary amine developing agent with a color coupler. Various patents describe techniques for improving the stability to light of the dyes making up the color images. Compounds which are effective to improve the light fastness of the co-existing dye include, for example, the hydroquinone derivatives disclosed in U.S. Pat. Nos. 2,360,290, 2,418,613, 2,675,314, 2,701,197, 2,704,713, 2,728,659, 2,732,300, 2,735,765, 2,710,801, and 2,816,028 and Brit. Pat. No. 1,363,921, etc., gallic acid derivatives set forth in U.S. Pat. Nos. 3,457,079 and 3,069,262, Published Japan. Pat. Appln. 13,496/1968, etc., p-oxyphenol derivatives set forth in U.S. Pat. Nos. 2,735,765, 3,432,300, 3,698,909, 3,573,050, 3,574,627 and 3,764,337, chroman and coumarane derivatives set forth in U.S. Pat. Nos. 3,432,300, 3,574,626, 3,698,909, 3,573,050 and 4,015,990, etc. These compounds certainly are effective to prevent fading or discoloration of dye images to a certain extent but not to a satisfactory extent.

Brit. Pat. No. 1,451,000 discloses that the stability of organic substrates to light is enhanced by the use of azomethine quenching compounds which have absorption maxima at a longer wavelength than the substrate materials. Unfortunately, the fact that the azomethine quenching compound is itself colored adversely affects the color hue of the substrate material.

Metal chelates can be used to prevent degradation of polymeric materials by the action of light as is described in the following literature; J. P. Guillory & R. S. Becker, _J. Polym. Sci._, Polym. Chem. Ed., 12, 993 (1974), R. P. R. Ranaweera & G. Scott, _J. Polym. Sci._, Polym. Let. Ed., 13, 71 (1975), etc. Stabilization of dyestuffs against light by the use of metal chelates is also described in U.S. Pat. No. 4,050,938, Japanese Patent Application (OPI) 87,649/1975 and Research Disclosure 15162 (1976). However, the disclosed metal chelates exhibit an unsatisfactory fade preventing effect, and when the metal chelates are employed in a photographic emulsion, as will be established by a comparative study later, the disclosed metal chelates desensitize the silver halide probably due to an undesirable interaction with silver. Also these metal chelates exhibit an undesirably poor solubility in organic solvents, which means the working concentration of such a chelate is too low to permit a sufficient fade prevention. Moreover, these chelates cannot be present in a high concentration since they themselves are colored and therefore adversely affect the color hue and the color purity of the dyes.

Furthermore, heretofore, agents suitable for preventing the fading of cyan dyes have not been known.

SUMMARY OF THE INVENTION

Accordingly, one object of the present invention is to stabilize organic substrates against the action of light.

Another object of the present invention is to improve the stability of organic substrates in particular, dyes or coloring agents to light without deteriorating their color hue as well as their color purity.

Still another object of the present invention is to enhance the stability of organic substrates to light by using stabilizing agents which are readily soluble in organic solvents and which are highly compatible with the organic substrates.

Another object of the present invention is to improve the stability to light of the dye images constituting color photographs.

Another object of the present invention is to improve the stability to light of dyestuffs formed by the reaction of an aromatic primary amine developing agent with a color coupler.

Still another object of the present invention is to improve the light fastness of colored polymers useful as agricultural vinyl cover sheets, umbrellas, tents, etc.

Another object of the present invention is to improve the light fastness of cyan dyes and especially cyan color photographic images.

These and other objects of the present invention will become more evident from the following description of the invention.

DETAILED DESCRIPTION OF THE INVENTION

The above mentioned and other objects of the present invention are achieved using at least one compound represented by the following general formula (I), which compound co-exists with the organic substrate.

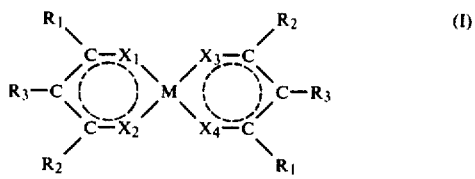

In the formula, M represents a metal atom selected from the group consisting of Cu, Co, Ni, Pd and Pt. $X_1$, $X_2$, $X_3$ and $X_4$ each represents an oxygen or a sulfur atom. $R_1$ and $R_2$ each represents an alkyl, an aryl, a cycloalkyl, an oxo-cycloalkyl or a heterocyclic group, each of which may be substituted or unsubstituted and attached to the carbon atom on the ring directly or through a divalent connecting group; $R_3$ represents a hydrogen atom, an alkyl, an aryl, a cycloalkyl, an oxocycloalkyl or a heterocyclic group, each of which may be substituted or unsubstituted and attached to the carbon atom on the ring directly or through a divalent connecting group. $R_1$, $R_2$ and $R_3$ may be the same or different; $R_1$ and $R_3$, or $R_2$ and $R_3$ may combine with each other to form a substituted or unsubstituted, 5-, 6- or 7-membered nucleus wherein $R_1$ and $R_3$, or $R_2$ and $R_3$ each represents a group of non-metallic atoms necessary to complete such a ring.

The terms "in the presence of" or "coexistant with" as used in the specification refer not only to co-existence of the substrate material and the compound of the formula (I) in the same solution, dispersion, emulsion or layer but also to the existence of the organic substrate and the complex in adjacent layers of a multi-layered photographic material. As long as the complex compound is associated with the organic substrate material such that it improves the light fastness of the organic substrate it is used "in the presence of" or "coexists" with the substrate for purposes of the present invention. The alkyl group represented by $R_1$, $R_2$ or $R_3$ is preferably a straight- or branched-chained alkyl group having 1 to 19 carbon atoms and may be substituted or unsubstituted including, for example, methyl, ethyl, propyl, butyl, hexyl, octyl, decyl, dodecyl, tetradecyl, hexadecyl and octadecyl. The aryl group represented by $R_1$, $R_2$ or $R_3$ may be monocyclic or bicyclic and preferably contains 6 to 14 carbon atoms and may be substituted or unsubstituted including, for example, phenyl and naphthyl. The heterocyclic group represented by $R_1$, $R_2$ or $R_3$ is preferably a 5- or 6-membered ring which may be substituted or unsubstituted. Preferably the heterocyclic group is a 5- or 6-membered group containing at least one hetero atom selected from the group consisting of nitrogen, oxygen and sulfur, and includes, for example, furyl, hydrofuryl, thienyl, pyrrolyl, pyrrolidinyl, pyridyl, piperidinyl, imidazolyl, imidazolidinyl, quinolyl, indolyl, indolinyl, oxazolyl, thiazolyl, morpholinyl, etc. The cycloalkyl group represented by $R_1$, $R_2$ or $R_3$ is preferably a 5- or 6-membered ring and may be substituted or unsubstituted. The cycloalkyl group represented by $R_1$, $R_2$ or $R_3$ is preferably a 5- or 6-membered group and includes, for example, cyclopentyl, cyclohexyl, cyclohexenyl, cyclohexadienyl, etc. The oxocycloalkyl group represented by $R_1$, $R_2$ or $R_3$ includes 2-oxocyclopentyl, 2-oxo-cyclohexyl, etc. The 5-, 6- or 7-membered nucleus formed by $R_1$ and $R_2$ or by $R_2$ and $R_3$ may be substituted or unsubstituted. The 5-, 6- or 7-membered nucleus completed by joining $R_1$ and $R_3$ or $R_2$ and $R_3$ include, for example, isocyclopentane, cyclohexane, cycloheptane, benzene, condensed benzene nuclei, etc.

The above described alkyl, cycloalkyl, oxo-cycloalkyl, aryl or heterocyclic group represented by $R_1$, $R_2$ or $R_3$ may be connected to the carbon atom on the ring through a divalent connecting group such as an oxy group (—O—), a thio group (—S—), or an amino group.

When $R_1$, $R_2$ or $R_3$ is an alkyl group and attached to the carbon atom on the chelated ring through one of the above-cited, divalent oxy, thio or amino group the substituents on the carbon atom on the chelated ring, in other words the substituents formed by the divalent connecting group and the alkyl group are illustrated by an alkoxy group, for example, methoxy, ethoxy, butoxy, propoxy, n-decyloxy, n-dodecyloxy, n-hexadecyloxy, etc.; an alkylamino group e.g., n-butylamino, N,N-diethylamino, N,N-didecylamino, etc.

When a cycloalkyl group represented by $R_1$, $R_2$ or $R_3$ is attached to the carbon atom on the chelate ring through one of the above-cited, divalent connecting groups the substituents on the chelate ring are exemplified by groups such as cyclohexyloxy cyclohexylamino, etc.

The substituents when the oxo-cycloalkyl group represented by $R_1$, $R_2$ or $R_3$ is attached to the carbon atom on the chelate ring through one of the above-cited, divalent connecting groups are exemplified by 2-oxocyclohexyloxy, 2-oxo-cyclopentyloxy, etc.

The substituents when the aryl group represented by $R_1$, $R_2$ or $R_3$ is bonded to the carbon atom on the chelate ring through one of the above-cited, divalent connecting groups are exemplified by an aryloxy group, e.g., phenoxy, naphthoxy, etc.; an anilino group, e.g., phenylamino, N-methylanilino, N-acetylanilino, etc.

The alkyl, aryl, cycloalkyl, oxo-cycloalkyl and heterocyclic groups represented by $R_1$, $R_2$ and $R_3$ may contain the following substituents; a halogen atom (Cl, Br or F, etc.), a cyano group, a straight- or branched-chain $C_1$–$C_{20}$ alkyl group, e.g., methyl, ethyl, propyl, butyl, hexyl, octyl, decyl, dodecyl, tetradecyl, hexadecyl, heptadecyl, octadecyl, etc.; an aryl group, e.g., phenyl, tolyl, naphthyl, chlorophenyl, methoxyphenyl, acetylphenyl, etc.; an alkoxy group, e.g., methoxy, ethoxy, butoxy, propoxy, etc.; an aryloxy group, e.g., phenoxy, tolyoxy, naphthoxy, etc.; an alkoxycarbonyl group, e.g., methoxycarbonyl, butoxycarbonyl, etc.; aryloxycarbonyl group, e.g., phenoxycarbonyl, tolyloxycarbonyl, etc.; an acyl group, e.g., formyl, acetyl, valeryl, stearoyl, benzoyl, toluloyl, naphthoyl, etc.; an acyloxy group, e.g., acetoxy, benzyloxy, toluoyloxy, etc.; an acylamino group, e.g., acetoamido, benzoylamido, etc.; an anilino group, e.g., phenylamino, N-methylanilino, N-phenylanilino, N-acetylanilino, etc.; an alkylamino group, e.g., n-butylamino, N,N-diethylamino, etc.; a carbamoyl group, e.g., n-butylcarbamoyl, N,N-diethylcarbamoyl, etc.; a sulfamoyl group, e.g., n-butylsulfamoyl, N,N-diethylsulfamoyl, n-didecylsulfamoyl, etc.; a sulfonylamino group, e.g., methylsulfonylamino, phenylsulfonylamino, etc.; and a sulfonyl group, e.g., mesyl, tosyl, etc.

Among the compounds represented by general formula (I) and characterizing the present invention, particularly, preferred are those represented by the following general formulae (Ia), (Ib) and (Ic).

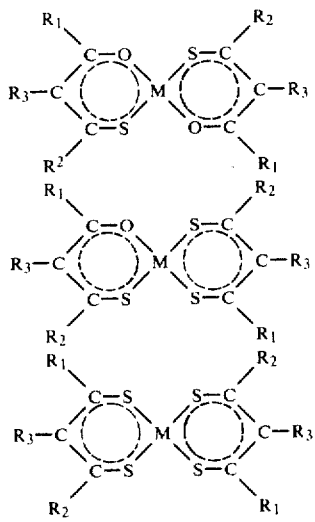

where M, $R_1$, $R_2$ and $R_3$ each represents the same groups as in general formula (I).

More specifically, particularly preferred compounds for the present invention represented by general formula (I) are those represented by the following general formulae (Id) and (Ie).

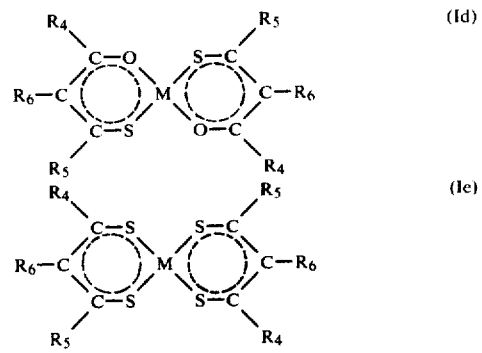

where M represents a metal selected from the group consisting of Cu, Co, Ni, Pd and Pt. $R_4$, $R_5$ and $R_6$ each represents an alkyl group having from 1 to 19 carbon atoms, e.g., methyl, ethyl, n-propyl, iso-propyl, n-butyl, tert-octyl, n-decyl, n-octyl, etc.; an alkoxy group having from 1 to 19 carbon atoms, e.g., methoxy, ethoxy, n-butoxy, n-decyloxy, n-dodecyloxy, etc.; an aryl group, e.g., phenyl, naphthyl, etc.; an aryloxy group, e.g., phenoxy, tolyloxy, etc.; an alkylamino group, e.g., N,N-diethylamino, N,N-didecylamino, etc.; an anilino group, e.g., phenylamino, tolylamino, etc.; a nitrogen containing heterocyclic group, e.g., pyrrolidinyl, piperidyl, etc.; or a halogen substituted alkyl group, e.g., trifluoromethyl, perfluoroethyl, etc.. $R_6$ may represent a hydrogen atom. $R_4$, $R_5$ and $R_6$ may be the same or different. Further, $R_4$ may combine with $R_6$, and $R_5$ may combine with $R_6$ to complete a benzene or cyclohexane ring.

The following structural formulae exemplify metal chelates (particularly suited) for the present invention and falling in the category represented by general formula (I).

EXAMPLES OF METAL CHELATE COMPOUND

| Compound No. | M | $X_1$ | $X_2$ | $X_3$ | $X_4$ | $R_1$ | $R_2$ | $R_3$ |
|---|---|---|---|---|---|---|---|---|
| I-1 | Ni | S | O | O | S | $CH_3$ | $CH_3$ | H |
| I-2 | Ni | S | S | S | O | $CH_3$ | $CH_3$ | H |
| I-3 | Ni | S | S | S | S | $CH_3$ | $CH_3$ | H |
| I-4 | Ni | S | O | O | S | $n\text{-}C_{12}H_{25}$ | $n\text{-}C_{12}H_{25}$ | H |
| I-5 | Ni | S | S | S | S | $n\text{-}C_{12}H_{25}$ | $n\text{-}C_{12}H_{25}$ | H |
| I-6 | Ni | S | S | S | S | $C_2H_5O^*$ | $CH_3$ | H |
| I-7 | Ni | S | S | S | S | $n\text{-}C_6H_{13}O^*$ | $CH_3$ | H |
| I-8 | Ni | S | S | S | S | $n\text{-}C_{12}H_{25}O^*$ | $CH_3$ | H |
| I-9 | Ni | S | O | O | S | $CH_3$ | $C_2H_5O^*$ | H |
| I-10 | Ni | S | O | O | S | $CH_3$ | $n\text{-}C_{18}H_{37}O^*$ | H |
| I-11 | Ni | S | S | S | S | $C_6H_5CH_2O^*$ | $C_6H_5CH_2O^*$ | H |
| I-12 | Ni | S | S | S | S | $n\text{-}C_4H_9O^*$ | $n\text{-}C_4H_9O^*$ | H |
| I-13 | Ni | S | O | O | S | $n\text{-}C_{10}H_{21}O^*$ | $n\text{-}C_{10}H_{21}O^*$ | H |
| I-14 | Ni | S | S | S | S | $n\text{-}C_{10}H_{21}O^*$ | $n\text{-}C_{10}H_{21}O^*$ | H |
| I-15 | Ni | S | S | S | S | $(C_2H_5)_2N^*$ | $CH_3$ | H |
| I-16 | Ni | S | S | S | S | $(n\text{-}C_{10}H_{21})_2N^*$ | $CH_3$ | H |
| I-17 | Ni | S | S | S | S | 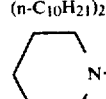 | $CH_3$ | H |
| I-18 | Ni | S | S | S | S | 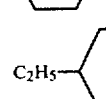 | $CH_3$ | H |
| I-19 | Ni | S | O | O | S | $CH_3$ | $CH_3$ | $CH_3$ |
| I-20 | Ni | S | O | O | S | $C_6H_5$ | $C_6H_5$ | $CH_3$ |
| I-21 | Ni | S | O | O | S | $C_6H_5$ | $C_6H_5$ | H |
| I-22 | Ni | S | S | S | S | $CF_3$ | $CF_3$ | H |
| I-23 | Co | S | O | O | S | $CH_3$ | $CH_3$ | H |

-continued

| Compound No. | M | $X_1$ | $X_2$ | $X_3$ | $X_4$ | $R_1$ | $R_2$ | $R_3$ |
|---|---|---|---|---|---|---|---|---|
| I-24 | Co | S | S | S | S | $CH_3$ | $CH_3$ | H |
| I-25 | Co | S | S | S | S | $C_6H_5$ | $CH_3$ | H |
| I-26 | Cu | S | S | S | S | $CH_3$ | $CH_3$ | H |
| I-27 | Cu | S | O | O | S | $CH_3$ | n-$C_{10}H_{21}O$* | H |
| I-28 | Pd | S | O | O | S | n-$C_{12}H_{25}O$* | n-$C_{12}H_{25}O$* | H |
| I-29 | Pd | S | S | S | S | n-$C_{12}H_{25}O$* | n-$C_{12}H_{25}O$* | H |
| I-30 | Pt | S | O | O | S | n-$C_{12}H_{25}O$* | n-$C_{12}H_{25}O$* | H |
| I-31 | Pt | S | S | S | S | n-$C_{12}H_{25}O$* | n-$C_{12}H_{25}O$* | H |

*including the connecting group

I-32

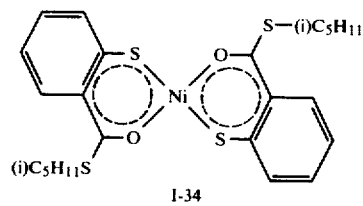

I-33

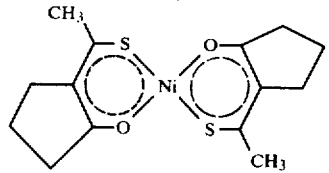

I-34

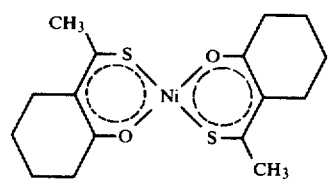

I-35

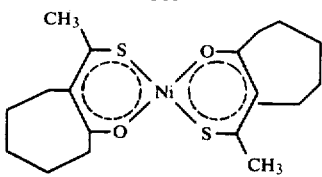

These metal chelates may be prepared by blowing HCl and $H_2S$ gas into a solution of a metal acetylacetonato complex in an organic solvent (methanol, ethanol, etc.), at room temperature for 10 to 24 hrs. under normal pressure. The reaction mixture is allowed to stand overnight. The crystal precipitated is separated, washed, dried, if necessary, recrystallized in a conventional manner. The details are described in the following literature; C. G. Barraclough, R. L. Martin and I. M. Stewart, Aust. J. Chem. 22, 891 (1969), and G. Barnikow and H. Kunzek, Z. Chem., 6, (1966).

SYNTHESIS EXAMPLE 1

Compound I-19

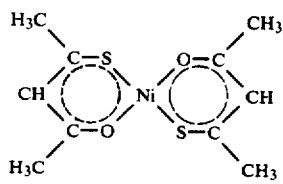

10 ml acetylacetone was added to a solution obtained by dissolving 5 g nickel carbonate in 80 ml of a 10 (wt) % alcohol solution of hydrogen chloride at 0° C. Gaseous hydrogen sulfide was vigorously bubbled through the mixture for about 2 hours. The temperature was then raised to the room temperature and gaseous hydrogen sulfide was slowly passed through the mixture for about 15 hours. A dark brown crystalline product precipitated, which was washed with cold methanol after filtration. The final product was recrystallized from hot methanol.

SYNTHESIS EXAMPLE 2

Compound I-32

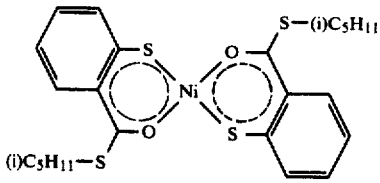

To a solution of 24 g S-iso-amyl-o-mercaptothiobenzoate in 50 ml ethanol was added dropwise with stirring a solution obtained by dissolving 30 g of nickel acetate quadrihydrate in 100 ml water at room temperature.

After the completion of the dropwise addition, stirring was continued for 10 minutes, and then the mixture was left stationary for 3 hours. A nickel complex precipitated which was separated by filtration, washed with water, and finally with ethanol.

The organic substrate material which can be used in conjunction with the present invention includes all those dyestuffs falling in the various categories classified from the viewpoint of textile dyeing; i.e., water-soluble dyes such as basic, acid, direct, water-soluble vat dyes, mordant dyes, etc., water-insoluble dyes such as sulfur, vat, oil-soluble, dispersion, azoic, oxidative dyes, etc., and reactive dyes. Not only compounds which appear colored under the illumination of sunlight, but also colorless or pale yellow compounds such as fluorescent whitening agents are included in the organic substrate material defined in the present invention.

Dyestuffs which are particularly suited for the application of the present invention include quinoneimine dyes (e.g., azine, oxazine, or thiazine dyes, etc.), methine or polymethine dyes (e.g., cyanine, azomethine, and other dyes), azo dyes, azomethine dyes, anthraquinone dyes, indoamine dyes, indophenol dyes, indigoid dyes, carbonium dyes, formazane dyes, etc., to be classified according to chemical structure, esp., functional groups thereof.

The organic substrate material treated in accordance with the present invention includes photographic images forming dyes including, for example, those produced from a color coupler, DRR (dye releasing redox) compound, DDR (diffusible dye releasing) coupler, amidolazone derivative dye developer, etc., those used for silver dye bleach process, etc.

More specifically, anthraquinone, quinoneimine, azo, methine, polymethine, indoamine, indophenol and formazane types of dyes are particularly suited for the practice of the present invention. Further, the present invention is most effective with dyestuffs which are methine and polymethine dyes, and indoamine and indophenol dyes, all of which have in their chemical structures a

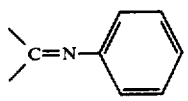

group. The phenyl group in the above expression may be substituted with an alkyl, an alkoxyl, a halogen, an amino group, etc.

Dye forming couplers used in the present invention include those capable of providing of yellow, cyan and magenta dye images. Such couplers are well known and may be of the so-called 4 equivalent or 2 equivalent type disclosed in, for example, U.S. Pat. Nos. 3,277,155 and 3,458,315.

In general, yellow dye forming couplers have at least one methylene group activated by a carbonyl group (e.g., an openchain ketomethylene group), including β-diketone, β-ketoacylamide such as benzoylacetanilide and α-pivalylacetanilide. Dye-forming couplers of this type are set forth in, for example, U.S. Pat. Nos. 2,428,054, 4,026,706, 2,499,966, 2,453,661, 2,778,658, 2,908,573, 3,227,550, 3,253,924, 3,277,155 and 3,384,657 and Brit. Pat. No. 503,572.

Magenta dye forming couplers exemplified by 5-pyrazolone derivatives can be used in conjunction with the present invention. This type of coupler is described in, for example, U.S. Pat. Nos. 2,600,788, 2,725,292, 2,908,573, 3,006,759, 3,062,653, 3,152,896, 3,227,550, 3,252,924, 4,026,706 and 3,311,476.

Other types of magenta dye forming couplers are indazolone derivatives such as described in Vittum & Weissberger "Journal of Photographic Science" 6, (1958), pp 158; U.S. Pat. No. 3,061,432 discloses pyrazolinobenzimidazole derivatives. Also included are pyrazolo-s-triazoles set forth in Belg. Pat. No. 724,427, and 2-cyanoacetylcoumarones set forth in U.S. Pat. No. 2,115,394.

Cyan dye forming couplers within the ambit of the present invention include phenol and α-naphthol derivatives which can form dyestuffs of indoaniline type upon the reaction with the oxidized color developer. Such derivatives are disclosed in U.S. Pat. Nos. 2,275,292, 2,423,730, 2,474,293, 2,895,826, 2,908,573, 3,043,892, 4,026,706, 3,227,550 and 3,253,294.

General descriptions of these coupler compounds are also found in, for example, "Encyclopedia of Chemical Technology" authored by Kirk and Othmer, Vol. 5, pp 822–825, and "Photographic Chemistry" authored by Glafkides, Vol. 2, pp 596–614.

As discussed earlier, the method of the present invention may be practiced for the dyestuffs obtained from such couplers by the reaction thereof with the oxidation product from a primary aromatic amine developer for silver halide. Such developing agents include aminophenol as well as phenylenediamine, each of which can be used individually or in mixed forms.

Typical developing agents which can react with various couplers to give organic substrate materials of the present invention include the following:

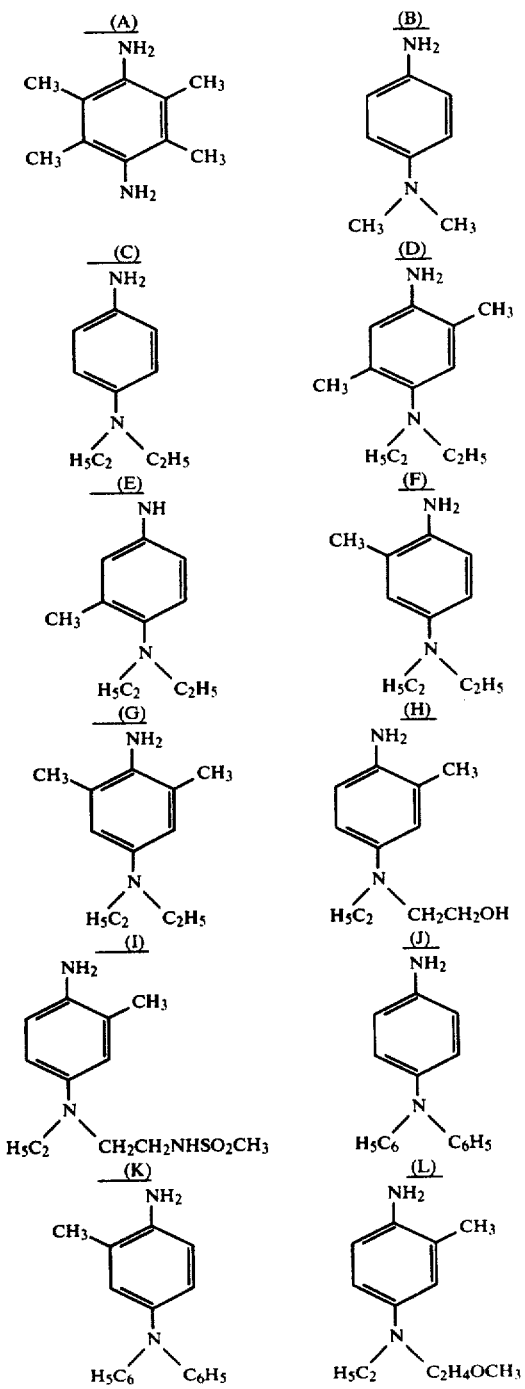

The developing agents illustrated above and others can provide organic substrates upon the reaction with photographic color couplers. Cyan, Magenta and Yellow Couplers which are preferably employed are represented by the formulae (IIa), (IIb) or (IIc) below respectively:

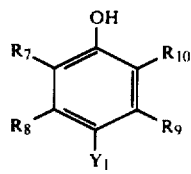
(IIa)

wherein $R_7$, $R_8$, $R_9$ and $R_{10}$ each represents a hydrogen atom, a halogen atom (e.g., fluorine, chlorine, bromine or iodine), an alkyl group having 1 to 20 carbon atoms (hereafter, all of the alkyl groups referred to with respect to formulae IIa, IIb and IIc may possess 1 to 20 carbon atoms) (e.g., methyl, ethyl, octyl, dodecyl, tetradecyl, octadecyl, etc.); an alkyl- or aryl-substituted carbamoyl wherein the aryl moiety has 6 to 10 carbon atoms, (hereafter all of the aryl groups referred to with respect to formulae IIa, IIb and IIc may possess 6 to 10 carbon atoms) (e.g., methylcarbamoyl, ethylcarbamoyl, dodecylcarbamoyl, tetradecylcarbamoyl, octadecylcarbamoyl, N-phenylcarbamoyl, N-tolylcarbamoyl, etc.); an alkyl- or aryl-substituted sulfamoyl group (e.g., methylsulfamoyl, ethylsulfamoyl, dodecylsulfamoyl, tetradecylsulfamoyl, octadecylsulfamoyl, N-phenylsulfamoyl, N-tolylsulfamoyl, etc.); an alkyl- or aryl-substituted amido group (e.g., acetamido, butylamido, benzamido, phenacetamido, etc.); a sulfonamido group (e.g., benzenesulfonamido), a phosphoric acid amido group, a ureido group, etc.

$R_7$ and $R_8$ may combine with each other to form a six-membered carbocyclic ring (e.g., a benzene ring which may further be substituted with an alkyl or aryl group).

$Y_1$ represents a hydrogen atom, a halogen atom (e.g., fluorine, chlorine, bromine or iodine); or a group which is releasable upon the reaction with the oxidation product of a developing agent (e.g., an alkoxy group wherein the alkyl moiety has 1 to 20 carbon atoms; an aryloxy group wherein the aryl moiety has 6 to 10 carbon atoms; a sulfonamido group, a sulfonyl group, a carbamoyl group, an imido group, an aminosulfonyloxy group, an alkylcarbonyloxy group, an arylcarbonyloxy group, an alkylthio group, an arylthio group, a heterocyclic ring thio group, etc.; the details of which are well known in the art.

The alkyl, carbamoyl, sulfamoyl and amido groups expressed by $R_7$, $R_8$, $R_9$ and $R_{10}$, or the 6-membered ring formed by combining $R_7$ and $R_8$ with each other can also be substituted with other substituents, for example, an alkyl group (e.g., methyl, ethyl, propyl, octyl, dodecyl, tetradecyl, octadecyl, etc.); an aryl group (e.g., phenyl, tolyl, naphthyl, etc.); an aryloxy group (e.g., phenoxy, 2,5-di(t)-amylphenoxy, etc.); a halogen atom (e.g., chlorine, bromine, fluorine, etc.); and the like.

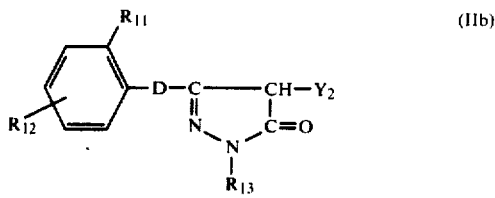
(IIb)

wherein $R_{11}$ represents a hydrogen atom, a halogen atom (e.g., chlorine, bromine, fluorine, etc.); an alkyl group (e.g., methyl, ethyl, n-propyl, etc.); or an alkoxy group (e.g., methoxy, ethoxy, etc.); $R_{12}$ represents an alkyl group (e.g., methyl, ethyl, octyl, dodecyl, tetradecyl, octadecyl, etc.); an amido group (e.g., butanamido, decanamido, tetradecanamido, nonadecanamido, etc.); an imido group (e.g., tetradecylsuccinimido, octadecenylsuccinimido, etc.); an N-alkylcarbamoyl group (e.g., decylcarbamoyl, tetradecylcarbamoyl, octadecylcarbamoyl, etc.); an N-alkylsulfamoyl group (e.g., decylsulfamoyl, tetradecylsulfamoyl, octadecylsulfamoyl, etc.); an alkoxycarbonyl group (e.g., decyloxycarbonyl, tetradecyloxycarbonyl, octadecyloxycarbonyl, etc.); an acyloxy group (e.g., valeryloxy, palmitoyloxy, stearoyloxy, oleyloxy, benzoyloxy, toluoyloxy, etc.); a sulfonamido group, a urethane group, etc. and $R_{13}$ represents an aryl group (e.g., phenyl, naphthyl, etc.) said alkyl and aryl groups having the number of carbon atoms discussed above with respect to formula IIa.

D represents an amino group, a carbonylamino group, or a ureido group.

$Y_2$ represents a hydrogen atom, a halogen atom (e.g., chlorine, bromine, etc.); or a group which is releasable upon reaction with the oxidation product with a developing agent (e.g., an arylazo group, an aryloxy group, an acyloxy group, an alkylthio group, an arylthio group, etc.). Such groups are well known.

The alkyl or alkoxy group represented by $R_{11}$, the alkyl amido, N-alkylcarbamoyl, N-alkylsulfamoyl, alkoxycarbonyl or acyloxy group represented by $R_{12}$, or the aryl group represented by $R_{13}$ can also be substituted with other substituents, for example, an alkyl group, an aryl group, an alkoxy group, an aryloxy group, an amido group, an N-alkylcarbamoyl group, an N-alkylsulfamoyl group, an acyloxy group, a carboxy group, a sulfo group, a halogen atom (e.g., chlorine, bromine, fluorine, etc.), or the like.

$$R_{14}-\underset{\underset{O}{\|}}{C}-\underset{\underset{Y_3}{|}}{CH}-\underset{\underset{O}{\|}}{C}-NH-R_{15} \quad \text{(IIc)}$$

wherein $R_{14}$ represents an alkyl group (e.g., methyl, ethyl, (t)-butyl), (t)-octyl, etc.) or an aryl group (e.g., phenyl) and $R_{15}$ represents an aryl group (e.g., phenyl).

$Y_3$ represents a hydrogen atom, a halogen atom (e.g., chlorine, bromine, etc.), or a group which is releasable upon reaction with the oxidation product of a developing agent, for example, a heterocyclic nuclei (e.g., naphthoimido, succinimido, 5,5-dimethylhydantoinyl, 2,4-oxazolidinedione residue, imido, pyridone residue, pyridazone residue, etc.), an acyloxy group, a sulfonyloxy group, an aryloxy group, a ureido group; which are well known in the art.

The alkyl or aryl group represented by $R_{14}$ and the aryl group represented by $R_{15}$ can also be substituted with other substituents, for example, an alkyl group, an aryl group, an alkoxy group, an aryloxy group, an amido group, an N-alkylcarbamoyl group, an N-alkylsulfamoyl group, an acyloxy group, a carboxy group, a sulfo group, a sulfonamido group, a halogen atom, etc.

The following couplers are illustrative however they are not to be construed as limiting the present invention.

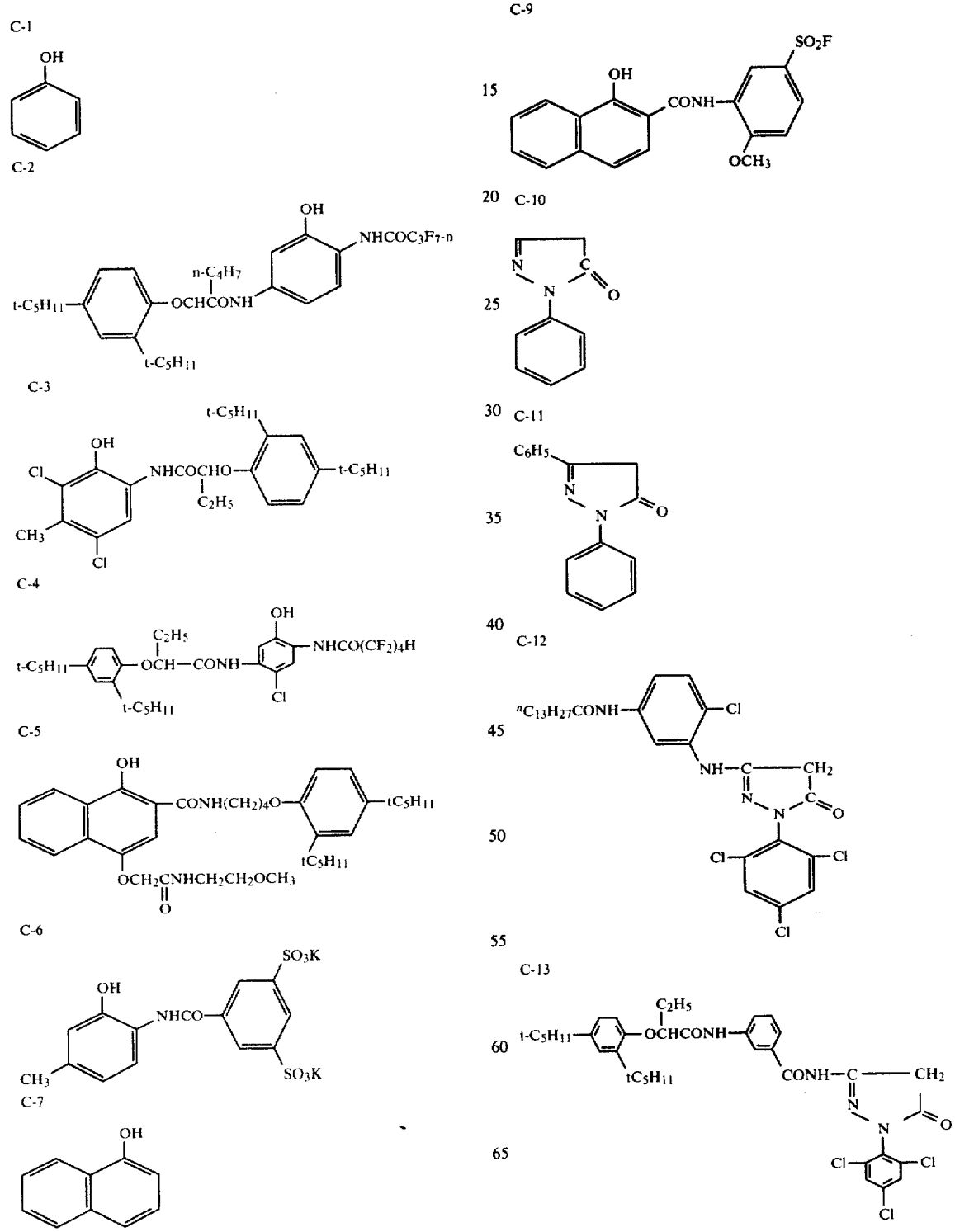

C-14
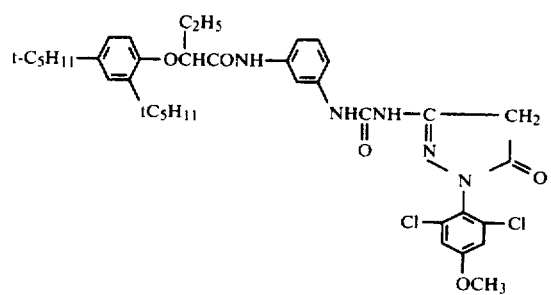
C-15
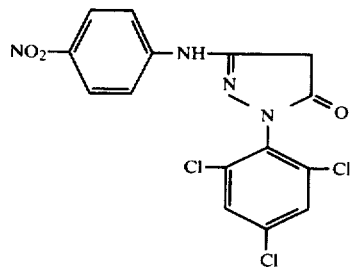
C-16
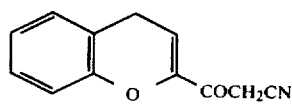
C-17  CN—CH₂—CN
C-18
C-19
C-20
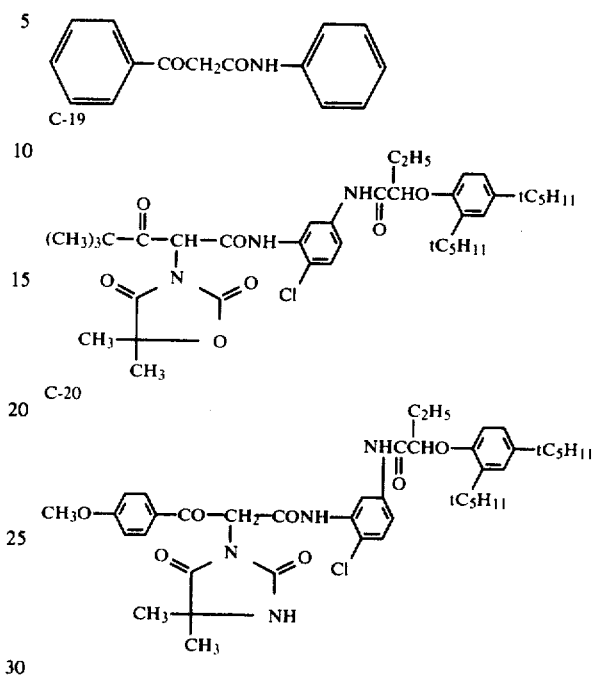
Other dyes to which the present invention is applicable are exemplified by the following compounds.
D-21
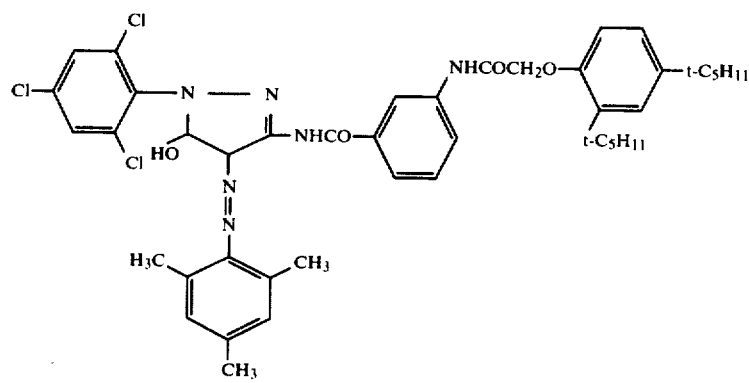
D-22
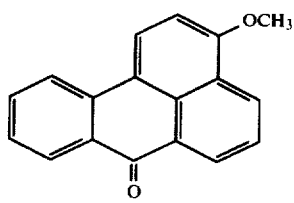
D-23
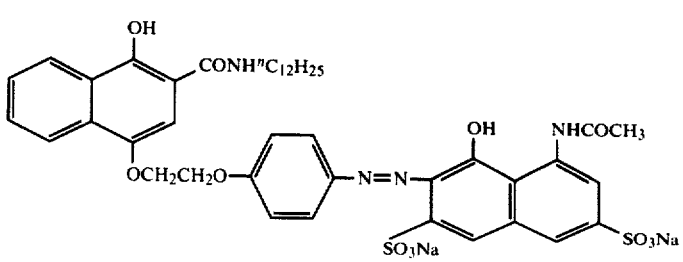

-continued
D-24
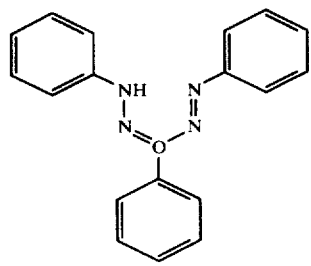
D-25
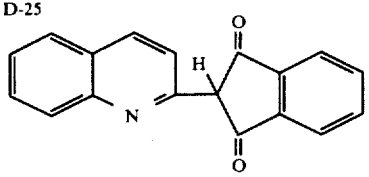
D-26
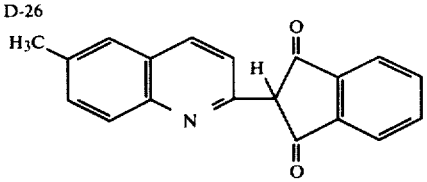
D-27
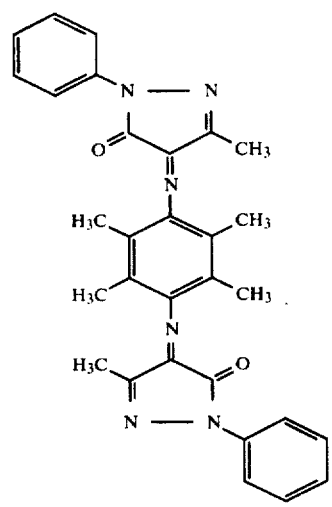
D-28
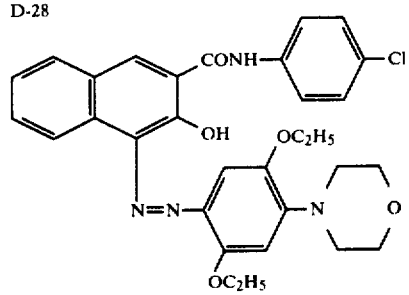
D-29
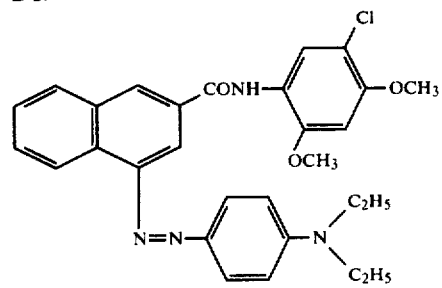
D-30
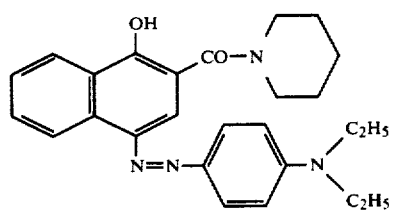
D-31
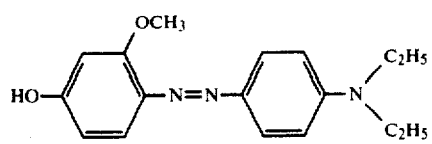
D-32
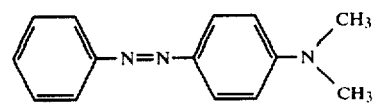

-continued
D-33
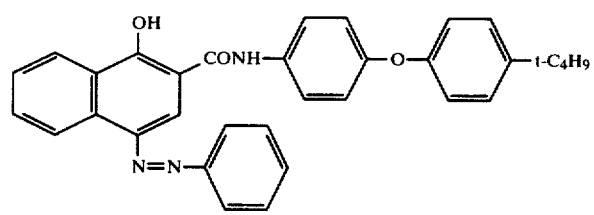
D-34
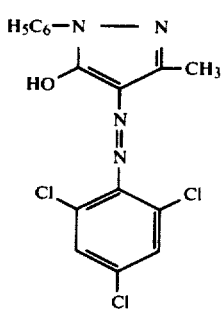
D-35
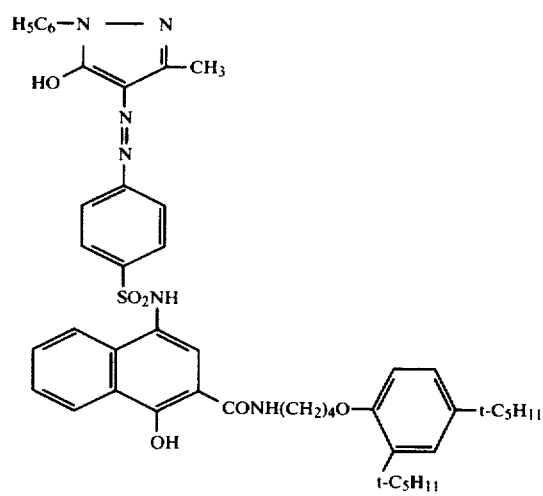
D-36
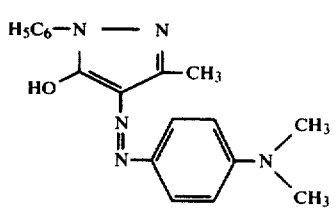
D-37
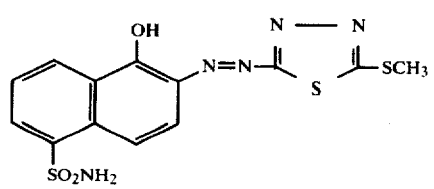
D-38
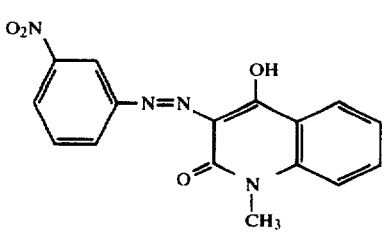
D-39
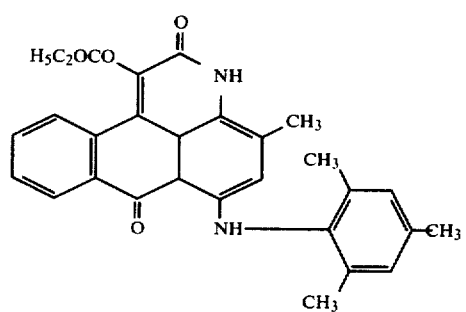
D-40
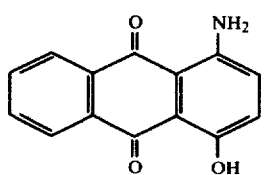

D-41
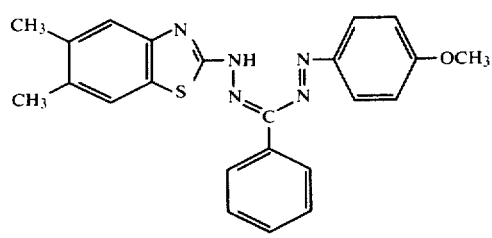
D-42
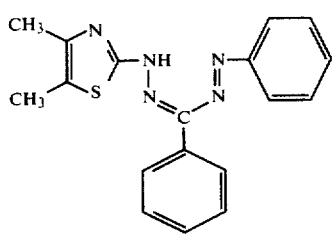
D-43
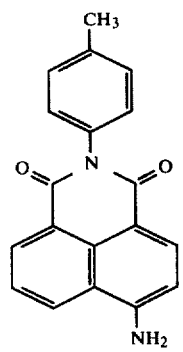
D-44
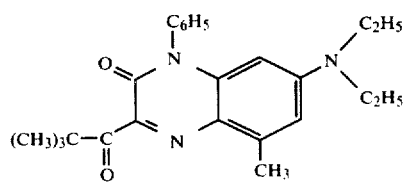
D-45
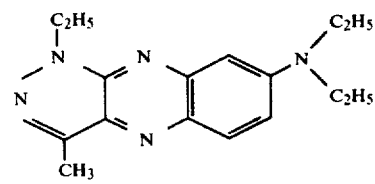
D-46
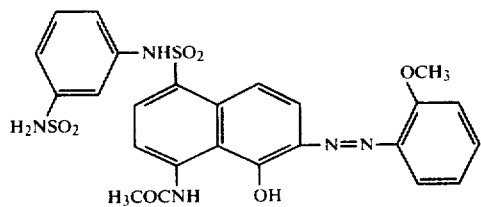
D-47
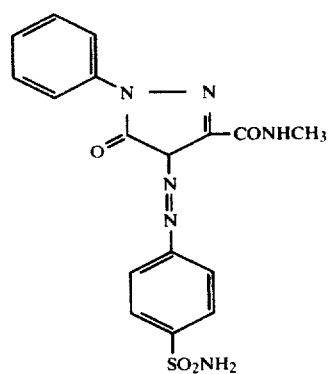
D-48
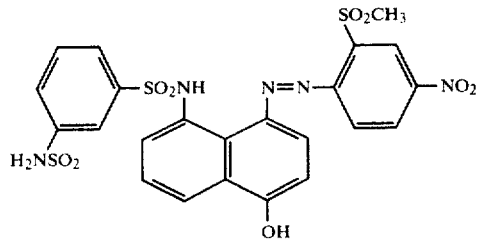
D-49
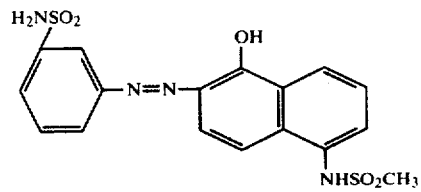

-continued
D-50
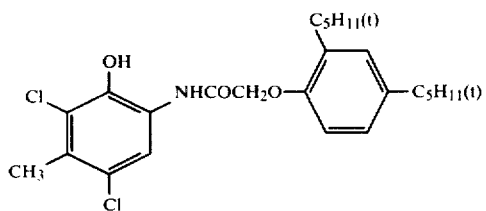
D-51
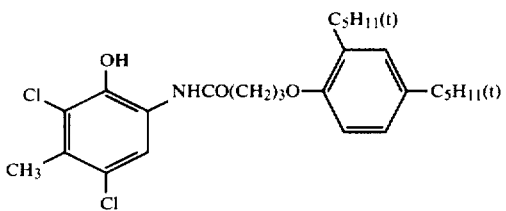
D-52
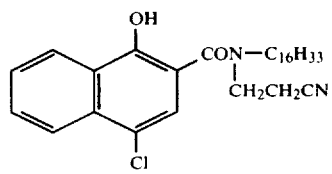
D-53
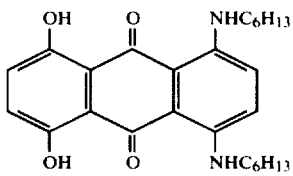
D-54
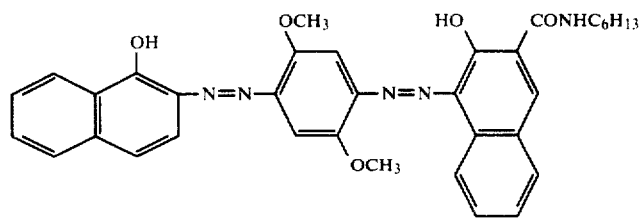
D-55
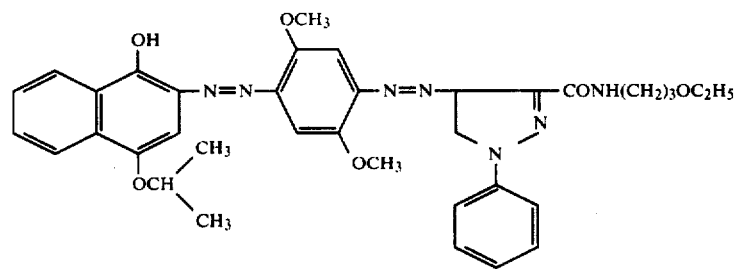
D-56
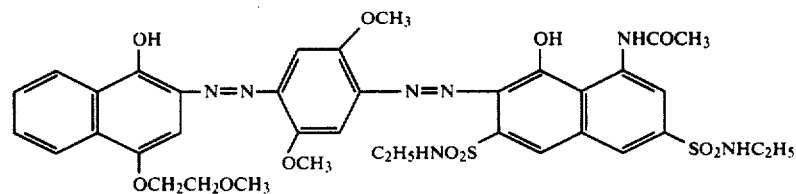
D-57
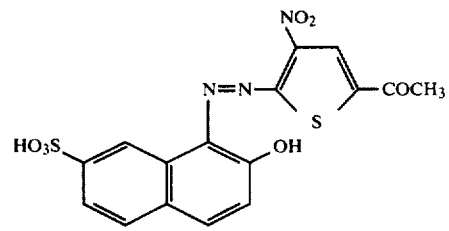
D-58
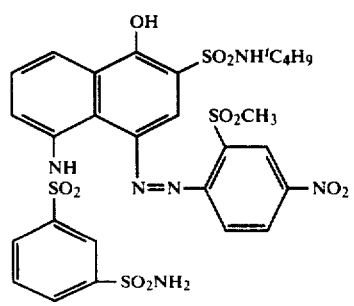

-continued
D-59
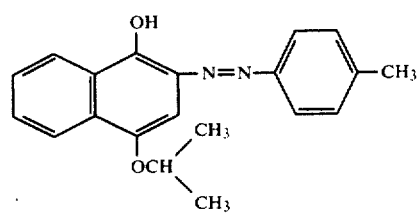
D-60
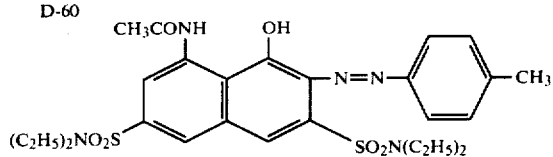
D-61
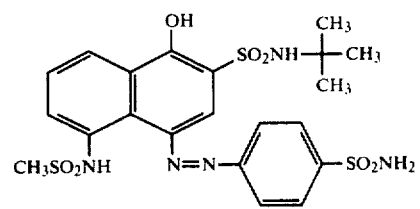
D-62
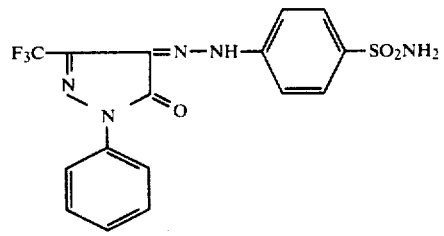
D-63
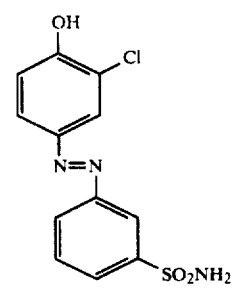
D-64
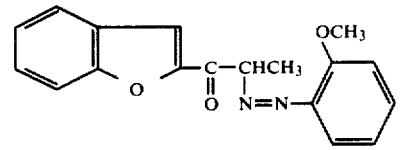
D-65
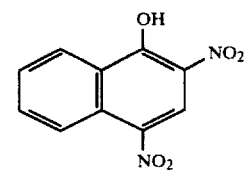
D-66
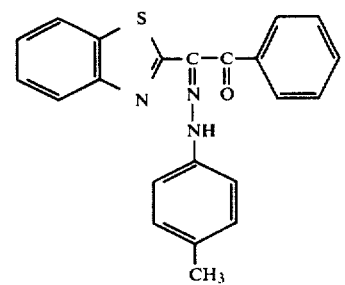
D-67
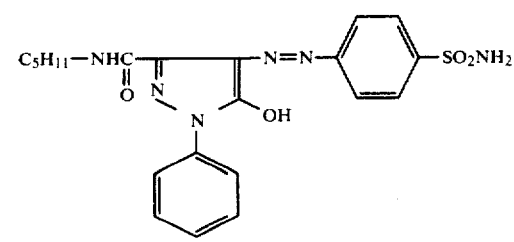
D-68
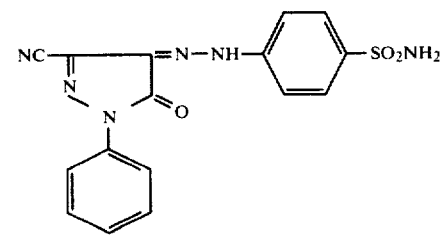

D-69

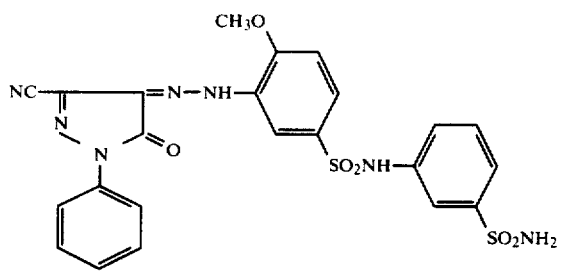

D-70

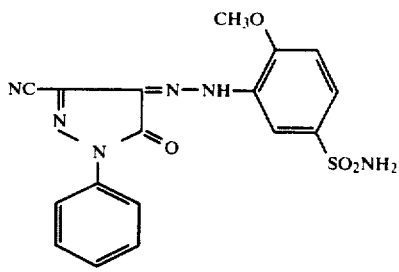

Still other types of dyes to which the teachings of the present invention can be preferably applied include those which are formed by the oxidation of DRR compounds described in the following patents and disclosure; U.S. B351,673 (U.S. Published Application), U.S. Pat. Nos. 3,932,381, 3,928,312, 3,931,144, 3,954,476, 3,929,760, 3,942,987, 3,932,380, 4,013,635 and 4,013,633, Japan. Pat. Appln. (OPI) 113,624/1976, 109,928/1976, 104,343/1976 and 4,819/1977, Japan. Pat. Appln. 64,533/1977 corresponding to OPI No. 149,328/78, "Research Disclosure" (1976 Nov.) pp. 68-74, No. 13024, etc.

Also, the present invention is applicable to those dyes which are released or formed as a result of reaction between DDR coupler and the oxidation product of a color developing agent; such DDR couplers are disclosed in, for example, Brit. Pat. Nos. 840,731, 904,364, 932,272, 1,014,725, 1,038,311, 1,066,352 and 1,097,064, Japan. Pat. Appln. (OPI) 133,021/1976, U.S. T900,029 (U.S. Defensive Publication), U.S. Pat. No. 3,227,550, etc.

The present invention is also applicable to dye developers set forth in Japan. Pat. Applns. (OPI) 182/1960, 18,332/1960, 32,130/1973, 43,950/1971 and 2,618/1974, etc.

Still other types of dye to which the present invention is applicable include those employed in silver dye bleach processes; yellow dyes are exemplified by azo dyes such as Direct Fast Yellow GC (C.I. 29000), Crysophenine (C.I. 24895), etc., benzoquinone dyes such as Indigo Golden Yellow IGK (C.I. 59101), Indigosol Yellow 2GB (C.I. 61726), Argosol Yellow GCA-CF (C.I. 67301), Indanthrene Yellow GF (C.I. 68420), Mikethrene Yellow GC (C.I. 67300), Indanthrene Yellow 4GK (C.I. 68405), etc., anthraquinone dyes, fused ring, soluble vat dyes, other types of vat dye, etc. Magenta dyes are exemplified by azo dyes such as Sumilite Supra Rubinol B (C.I. 29225), Benzobrilliant Gelanine B (C.I. 15080), etc., Indigoid dyes such as Indigosol Brilliant Pink IR (C.I. 73361), Indigosol Violet 15R (C.I. 59321), Indigosol Red Violet IRRL (C.I. 59316), Indanthrene Red Violet RRK (C.I. 67895), Mikethrene Brilliant Violet BBK (C.I. 6335), etc., soluble vat dyes comprising anthraquinone-hetero-polycyclic compounds, and other types of vat dye. Cyan dyes include zero dyes such as Direct Sky Blue 6B (C.I. 24410), Direct Brilliant Blue 2B (C.I. 22610), Sumilite Supra Blue G (C.I. 34200), etc., phthalocyanine dyes such as Sumilite Supra Turkeys Blue G (C.I. 74180), Mikethrene Brilliant Blue 4G (C.I. 74140), etc. Indanthrene Turkeys Blue 5G (C.I. 69845). Indanthrene Blue GCD (C.I. 73066), Indigosol O 4G (C.I. 73046), Anthrasol Green IB (C.I. 59826), etc.

The metal chelate complex associated with the present invention acts to stabilize organic substrate materials to light, and can be incorporated in at least one of the layer(s) making up the emulsion coating of a color photographic film product. The metal chelate compound can be present in any layer involved in the non light-sensitive portion of a color transfer material, e.g., a hydrophilic colloid layer, a protective layer, intermediate layers, a filter layer.

The substrate material and the complex each may be present in one or more of the hydrophilic colloid layers making up the photographic element. (film, paper diffusion transfer unit etc.). It is preferred that the metal chelate complex and the organic substrate material be present (i.e., coexist) in the same emulsion layer, of course, the effect of the present invention can also be attained when the complex and substrate are present in contiguous layers inasmuch as diffusion is allowed to occur between the layers. Were any (further) undesirable diffusion to occur, conventional mordanting techniques could be applied to the present invention. They may be present in a non-light-sensitive elements or layers as well, such as the dye image receiving layer used in diffusion transfer film units. In the case of image transfer units, the metal chelate complex is preferably located in a layer where dye images are finally found, i.e., in an image-receiving layer. Usually, the dye images formed in the image-receiving layer do not diffuse further into any other layer(s) so the complex is generally used in the image-receiving layer. In the case where the substrate material and the complex are contained in such a non light-sensitive layer or element, the complex and substrate are generally mordanted. In such a case, the chelate complex possesses an organic ligand suited for being held in the mordanted layer of the image receiving member so that the complex does not diffuse and leave the vicinity of the dye substrate to by stabilized. However, using the mordanting techniques effectively, the chelate complex can be incorporated in any other layer adjacent the image-receiving layer, as long as diffusion is effected and the chelate complex interacts with the dye images to improve light fastness.

A number of types of image transfer film units are particularly appropriate for the practice of the present invention. One is the imbibition transfer film unit set forth in U.S. Pat. No. 2,882,156. The present invention can be further used in conjunction with the color image transfer film unit described in U.S. Pat. Nos. 2,087,817, 3,185,567, 2,983,606, 3,253,915, 3,227,550, 3,227,551, 3,227,552, 3,415,646, 3,594,164 and 3,594,165 and Belg. Pat. Nos. 757,959 and 757,960.

Efficient methods of dispersing these metal chelates include those used for the dispersion of couplers. U.S.

Pat. Nos. 2,304,939 and 2,322,027 disclose the use of low-volatile organic solvents for the dissolution of metal chelates. Other methods suitable for this purpose include those described in U.S. Pat. Nos. 2,801,170, 2,801,171 and 2,949,360 wherein low-boiling point or water-soluble organic solvents are employed in conjunction with low-volatile solvents.

Low-volatile solvents effectively used for the dispersion of the organic substrate material as well the metal chelate used in the present invention include di-n-butyl phthalate, benzyl phthalate, triphenyl phosphate, tri-o-cresyl phosphate, diphenylmono-p-tert-butylphenyl phosphate, monophenyldi-p-tert-butylphenyl phosphate, diphenylmono-o-chlorophenyl phosphate, monophenyldi-o-chlorophenyl phosphate, 2,4-di-n-amylphenol, 2,4-di-t-amylphenol, N,N-diethyllaurylamide, trioctyl phosphate and trihexyl phosphate both of which are set forth in U.S. Pat. No. 3,676,137, etc.

Volatile and/or water-soluble organic solvents which can be used in conjunction with the above-cited low-volatile solvents are those described in, for example, U.S. Pat. Nos. 2,801,171, 2,801,170 and 2,949,360, including: (1) Solvents which are substantially immiscible with water such as methyl acetate, ethyl acetate, propyl acetate, butyl acetate, isopropyl acetate, ethyl propionate, sec-butyl alcohol, ethyl formate, butyl formate, nitromethane, nitroethane, carbon tetrachloride, chloroform, etc., and (2) Water-miscible organic solvents such as, for example, methyl isobutyl ketone, $\beta$-ethoxyethyl acetate, $\beta$-butoxytetrahydrofurfuryl adipate, diethylene glycol monoacetate, methoxytriglycol acetate, acetonylacetone, diacetone alcohol, ethylene glycol, diethylene glycol, dipropylene glycol, acetone, methanol, ethanol, acetonitrile, dimethylformamide, dioxane, etc.

The complex compound and the substrate material embodying the present invention can be used in conjunction with the materials described in "Product Licensing Index" Vol. 92, No. 9232 (1971, Dec.), pp. 107-110 according to the methods also described therein. Reference is made to Chapters, I, II, III, IV, V, VII, VIII, IX, X, XI, XII, XIII, XIV, XV, XVI, XVII, XVIII and XXIII.

In general, the complex of the formula (I) is dissolved or suspended in an appropriate solvent which is chosen, depending upon the physical properties of the complex used, from water, water-miscible and water-immiscible organic and inorganic solvents (the details of which are described in U.S. Pat. No. 3,966,468) and the organic substrate material is dissolved or suspended therein. Alternatively, again depending upon the physical properties of the compounds; solutions and/or dispersions may be prepared separately and subsequently mixed. For example, a fluorescent whitening agent may be dissolved or suspended in an organic or inorganic solvent such as water or dimethylformamide, etc. together with the complex of the present invention or separately; and the mixture may be coated onto or incorporated into a suitable base substance. An adjacent double layer coating is possible and in some cases may be preferred if some diffusion between the contiguous layers occurs and light fastness improvement is effected. Where it is desired to improve the light fastness in a colored polymer for use of agricultural vinyl sheets, the colored polymer and complex of the formula (I) are likewise mixed in the form of a solution, dispersion, etc., followed by extrusion molding, etc., in a conventional manner.

The colored polymer as used herein is a polymer containing a coloring material in a state of molecular dispersion or melt. The polymer is represented by natural resins other than gelatin, e.g., cellulose and derivatives thereof, vinyl resins, polycondensates, silicone resins, alkyl resins, polyamides, paraffin and mineral waxes as described in U.S. Pat. No. 3,966,468.

Any amount of the complex will bring about some improvement in the light fastness of the organic substrate and there is no upper limit for the amount of the complex from a theoretical standpoint. Preferably, the complex is present in an amount of at least 0.1 mol % based on 1 mol of the organic substrate material, more preferably, in an amount of 0.1 to 1000 mol %, and most preferably, in an amount of 1 to 300 mol %. In the case of a photographic material, the amount is often expressed in a weight unit per square meter of photographic material which can be calculated from the parameters set out above. For convenience, however, in the case of a photographic material, the complex is preferably present in an amount of at least 1 micromole per square meter of the photographic material, and more preferably in an amount of from about 10 to $1 \times 10^4$ micromoles per square meter of the material. The concentration of the substrate material corresponds in general to that for the image forming material usually adopted in color photographic technology. As is well known to those skilled in the art, the substrate material is preferably present in the range of from about 10 to $10^3$ micromoles per square meter of the photographic material. A more preferable range is from about 100 to about $3 \times 10^3$ micromoles per square meter of the photographic product.

The substrate materials which are the object of the present invention, usually have the maximum absorption peak at an wavelength shorter than about 800 nm. This peak should preferably be in the range of from about 300 to 800 nm, and more preferably from about 400 to 800 nm.

Any types of support material ordinarily used in photograhic products can be used in the present invention, including, for example, cellulose nitrate film, cellulose acetate film, cellulose acetate butyrate film, cellulose acetate propionate film, polystyrene film, poly(ethylene terephthalate) film, polycarbonate film, laminated sheet materials comprising the above-mentioned films, paper, etc. Especially suited ones are baryta coated paper, paper laminated or coated with an $\alpha$-olefin polymer such as polyethylene, polypropylene and other polymers comprising $C_2$–$C_{10}$ $\alpha$-olefins, those plastic films disclosed in Publd. Japan. Pat. Appln. 19,068/1972 which are provided with a roughened surface of an improved adhesive property to other polymeric materials, etc.

To prepare a photographic light-sensitive material used for the present invention, various hydrophilic colloids are employed. Hydrophilic colloid materials used as the binder for the photographic emulsion coating and/or other elementary coatings include, for example, gelatin, colloidal albumin, casein, cellulose derivatives such as carboxymethylcellulose, hydroxyethylcellulose, etc., carbohydrate derivatives such as agar-agar, sodium alginate, starch and its derivatives, etc., synthetic hydrophilic polymers such as poly(vinyl alcohol), poly(N-vinylpyrrolidone), acrylic acid containing copolymers, maleic anhydride containing copolymers, polyacrylamide, derivatives from these synthetic polymers including partially hydrolyzed products thereof, etc. If necessary, two or more of these colloidal materials are use in combination provided that they are compatible with each other.

Among these, most extensively used in gelatin, which can be replaced totally or partially with synthetic polymeric materials or with the so-called gelatin derivatives well known in the art. Such gelatin derivatives can be prepared by the modification or treatment of gelatin with reagents which have a functional group capable of reacting with the reactive groups contained in the gelatin molecule such as amino group, imino group, hydroxy group, or carboxy group, or by grafting to the gelatin molecule a suitable, synthetic polymer chain.

The photographic emulsion coating or other additional coatings composing the photographic product used for the present invention can involve synthetic polymer materials such as, for example, a latex of vinyl polymer dispersed in water and those which can improve the dimensional stability of the finished product. The photographic product can contain one or more of such polymeric materials, and, in some cases, in conjunction with a hydrophilic, water-permeable colloid.

Silver halide photographic emulsions used in the present invention are usually prepared by mixing an aqueous solution of a water-soluble silver salt (e.g., silver nitrate) with an aqueous solution of a water-soluble halide (e.g., potassium bromide) under the presence of a water-soluble polymeric material such as gelatin. The resulting silver halide includes not only silver chloride and silver bromide, but those containing halogen mixtures such as chlorobromide, iodobromide, chloroiodobromide, etc. Any methods well known in the art can be adopted to prepare such a grains of silver halide, including self-evidently single and double jet methods, control double jet method, etc. One can also blend two or more kinds of silver halide photographic emulsion each of which has been prepared independently.

A number of additives can be incorporated in the photographic emulsion in order to prevent the deterioration of photographic speed or the generation of fog during the manufacturing operation, the storage period and photographic processing operation. Such additives include various heterocyclic compounds such as 4-hydroxy-6-methyl-1,3,3a,7-tetrazaindene, 3-methylbenzothiazole, 1-phenyl-5-mercaptotetrazole, etc., Hg containing compounds, mercapto compounds, metal salts, etc.

The photographic emulsion used in the present invention can be chemically sensitized according to one of the known methods. Chemical sensitizers include gold compounds such as chloroaurates, gold trichloride, etc., salts of noble metals such as Pt, Pd, Ir, Rd, etc., those sulfur compounds that can react with silver salts to yield silver sulfide (e.g., sodium thiosulfate), and other reducing substances such as stannous salt, amine, etc.

The photographic emulsion used in the present invention can be spectrally sensitized or super-sensitized by the use of cyanine dyes such as cyanine, merocyanine, carbocyanine individually or assortedly among themselves or with styryl type dyes. The selection of dyes depends on the spectral region to be sensitized, the degree of spectral sensitivity, etc., vary with the desired application for the resulting photographic product.

The hydrophilic colloid contained in the photographic material used in the present invention can be, if desired, cross-linked with a variety of hardening agents such as, for example, aldehydes, active halogen compounds, vinylsulfone compounds, carbodiimide compounds, N-methylol compounds, epoxy compounds, etc.

According to one embodiment of the instant invention where the method of the invention is applied to a color photographic material, the color photographic material is, after imagewise exposure, processed in an ordinary manner to provide color images. Such processing comprises color development, bleaching and fixing to which other steps such as washing with water or stabilization may be introduced if necessary. Some of these processing operations can be united into a monobath step; a typical example is the so-called "blix" comprised of bleaching and fixing. The color development is carried out in an alkaline solution containing an aromatic primary amine developing agent. Preferable compounds as the developing agent include Compounds (A) to (L) already illustrated in the specification.

In other embodiment the method of the instant invention is applied to a diffusion transfer color photographic product type. In this case the processing is effected within the photographic material automatically. Suitable developing agents which are contained in a rupturable container include, in addition to Compounds (A) to (L), N-methylaminophenol, 1-phenyl-3-pyrazolidone, 1-phenyl-4,4-dimethyl-3-pyrazolidone, 1-phenyl-4-methyl-hydroxymethyl-3-pyrazolidone, 3-methoxy-N,N-diethyl-p-phenylenediamine, etc.

For the formation of color images in the photographic material used in the instant invention, the following methods can be employed; One based on the coupling reaction between a dye-forming color coupler and the oxidation product from a p-phenylenediamine type chromogenic developing agent; one using dye developers; one based on the oxidative cleavage reaction of a DRR compound; one based on the dye-releasing reaction resulting from the coupling reaction of a DDR coupler; one based on a dye-forming reaction caused by the coupling reaction of a DDR coupler; silver dye bleach process and other conventionally known ones.

As is evident from the above description, the method of the instant invention can be applied to a wide variety of color photographic materials such as color positive film, color printing paper, color negative film, color reversal film, film units for color diffusion transfer, silver dye bleach photographic material, etc.

EXAMPLE 1

Into a mixture comprising 3 ml trinonyl phosphate and 5 ml ethyl acetate was dissolved 0.1 g of a dye having the following structure.

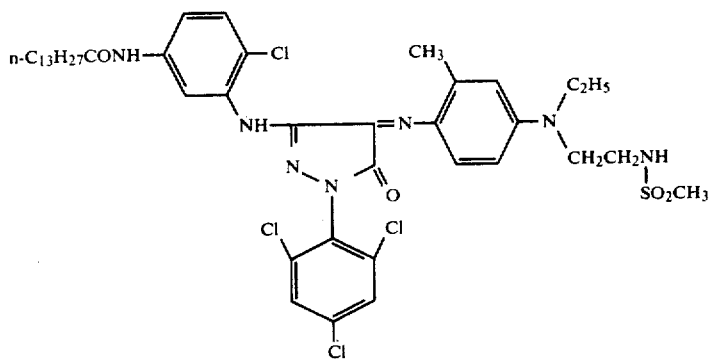

The resulting solution was emulsified into 10 g of a 10% aqueous gelatin solution containing 1 ml of a 1% sodium dodecylbenzenesulfonate solution.

This emulsified dispersion was mixed with 10 g of a 10% gelatin solution and then spread onto a substrate comprising a paper support laminated with polyethylene films on both surfaces and dried to give Sample A.

Another sample (Sample B) was prepared in a similar manner except that 50 mg of Compound I-1 characteristic of the instant invention was added to the emulsified dispersion. Furthermore, Samples C and D are prepared similarly but with the addition of 2,5-di-tert-octyl hydroquinone (a conventional fade prevention agent) in an amount of 0.02 g for C and of 0.2 g for D, respectively.

The coating rate of the dye was 60 mg/m² and the coating rate of Compound I-1 was 30 mg/m².

A 48 hour fading test was carried out on pieces of these samples superimposed with a UV cut filter C-40 produced by Fuji Photo Film Co., in a Xenon Tester (Light intensity; 200,000 luxes).

The results of the test obtained by the measurements with Macbeth Densitometer RD 514 provided with a green filter of status AA grade are shown in Table 1.

TABLE 1

| Sample | Initial density | Density after 48 hour fading test |
|---|---|---|
| A | 0.80 | 0.02 |
| B | 0.78 | 0.70 |
| C | 0.80 | 0.08 |
| D | 0.82 | 0.50 |

The results reveal the superior effect of the chelate complex of the present invention in fade prevention in comparison with the conventionally known fade preventing agents used in Samples C and D. It should be noted that in Samples B and C equivalent moles of the fade preventing agents are present. Comparison of B and D shows that even ten times amount of the conventional fade preventing agent is less effective than the complex composing the instant invention.

EXAMPLE 2

0.1 g of Compound D-23 was mixed with 2 ml of 1 N NaOH and then added to 2 ml methanol. The solution obtained was added to 10 g of a 10% gelatin solution. The resulting mixture was coated on a substrate comprising a paper support laminated on both sides with polyethylene film in such a manner that the coating rate of Compound D-23 was 80 mg/m² to prepare a Sample E.

In a similar manner Sample F was prepared by the addition of Compound I-3, characteristic of the present invention in an amount of 50 mg. Sample G was prepared for comparison by the addition of 100 mg of the compound having the following structure.

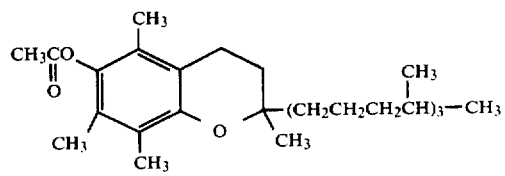

A 15 hour fading test was carried out as in Example 1 using the same UV cut filter. The results are shown in Table 2.

TABLE 2

| Sample | Initial density | Density after 15 hour fading test |
|---|---|---|
| E | 0.90 | 0.03 |
| F | 0.88 | 0.55 |
| G | 0.90 | 0.10 |

A Macbeth Densitometer was again used for density measurement.

Table 2 clearly mainfests the excellent effect of the compound characterizing the present invention for fade prevention.

EXAMPLE 3

10 g of a magenta coupler, 1-(2,4,6-trichlorophenyl)-3-[2-chloro-5-tetradecanamide]anilino-2-pyrazolino-5-one was dissolved in a mixture consisting of 30 ml trioctyl phosphate, 5 ml dimethylformamide and 15 ml ethyl acetate, and the resulting solution was emulsified in 80 g of a 10% gelatin solution containing 8 ml of a 1% aqueous sodium dodecylbenzenesulfonate solution. The dispersion was mixed with 145 g of a green sensitive silver chlorobromide emulsion which contained 7 g of silver chlorobromide halide (bromide content in the silver halide was 70 mole %). After the addition of a hardening agent and a coating aid, the mixture was spread over a substrate comprising a paper support laminated on both sides with polyethylene film to give Sample H. The coating rate of the coupler was 400 mg/m².

By repeating the procedure, Samples I and J were prepared in which Compound 1-2 of this invention was added for Sample I in an amount of 0.5 g and a coating amount of 20 mg/m² while 2.0 g of the following compound was used for Sample J for a coating amount of 80 mg/m².

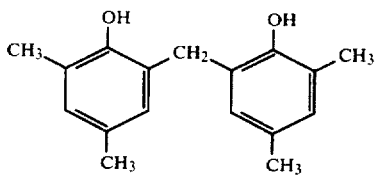

After exposure, each of these samples was processed with the following processing solutions.

| Developer | |
|---|---|
| Benzyl alcohol | 15 ml |
| Diethylenetriamine pentaacetate | 5 g |
| KBr | 0.4 g |
| $Na_2SO_3$ | 5 g |
| $Na_2CO_3$ | 30 g |
| Hydroxylamine hydrosulfate | 2 g |
| 4-Amino-3-methyl-N-ethyl-N-$\beta$-(methane-sulfonamide)ethylaniline 3/2$H_2SO_4$ . $H_2O$ | 5 g |
| Water to make | 1000 ml |
| pH | 10.1 |
| Blix solution | |
| Ammonium thiosulfate (70 wt %) | 150 ml |
| $Na_2SO_3$ | 5 g |
| Na[Fe(EDTA)] | 40 g |
| EDTA | 4 g |
| Water to make | 1000 ml |
| pH | 6.8 |
| Processing conditions | |
| Development | 33° C., 3 min. 30 sec. |
| Blix | 33° C., 1 min. 30 sec. |
| Washing with water | 28–35° C., 3 min. |

Each sample bearing a dye image was exposed to sunlight for 2 weeks through a UV cut filter C40 (a product of Fuji Photo Film Co.) which eliminates light having a wavelength shorter than 400 m$\mu$.

The results are listed in Table 3. The degree of fading was expressed by the density drop at the area with the initial density of 2.0. The density was measured with a Macbeth Reflective Densitometer TCD 514 (status AA filter).

TABLE 3

| Sample | Density drop by fading test (%) | |
|---|---|---|
| H | 80 | comparison |
| I | 15 | invention |
| J | 50 | comparison |

The table shows the superior fade retarding effect of the complex compound of the present invention.

EXAMPLE 4

Into a mixture of 1 ml trioctyl phosphate and 5 ml ethyl acetate were dissolved 0.1 g of the dye employed in EXAMPLE 1 and 5 mg of Compound I-1 of the instant invention.

The resulting solution was emulsified into 10 g of a 10% aqueous gelatin solution containing 1 ml of a 1% sodium dodecylbenzenesulfonate solution.

The so-emulsified dispersion was mixed with 10 g of a 10% gelatin solution and then spread onto a substrate comprising a paper support laminated with polyethylene film on both surfaces and dried to obtain Sample A.

Another sample (Sample B) was prepared in a similar manner except that 5 mg of Compound IV described in U.S. Pat. No. 4,050,938, having the following structure;

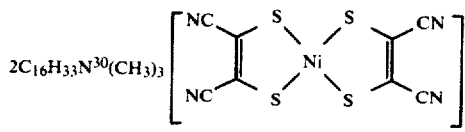

was used in place of Compound I-1.

The coating rates were as follows:

| Dye | 60 mg/m$^2$ |
|---|---|
| Compound I-1 Compound IV (for comparison) | 3 mg/m$^2$ |

A 48 hour fading test was carried out in a manner similar to Example 1. The results are shown in Table 4.

TABLE 4

| Sample | Initial density | Density after 48 hour fading test |
|---|---|---|
| A | 0.80 | 0.78 |
| B | 0.85 | 0.05 |

As can be clearly understood from the results shown in the above table, the chelate complex of the present invention exhibits far superior light fastness to the chelate complex of the prior art.

EXAMPLE 5

A solution of 50 mg of a dye having the structure below 500 mg of polycarbonate Lexan 145 (tradename, manufactured by General Electric Co.) in 100 ml of dichloromethane was coated onto a glass plate using a spinner. A film of 5.5 $\mu$m thick which was magenta-colored was thus prepared as Sample A.

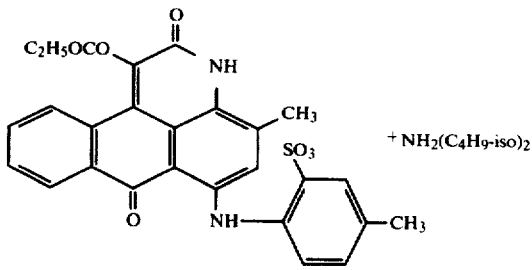

In a similar manner, a colored film was prepared as Sample B except that Compound I-1 of the instant invention was further incorporated into the solution.

The coating rates of the dye and the fade prevention compound were 500 mg/m$^2$ and 50 mg/m$^2$, respectively.

The thus obtained film were exposed to sunlight for one month and a color fading test was carried out.

The results obtained are shown in Table 5, in which the density was measured at 550 nm.

TABLE 5

| Sample | Initial density | Density after fading |
|---|---|---|
| A | 1.0 | 0.50 |
| B | 1.0 | 0.90 |

It can be clearly understood from the results shown in the foregoing table that the system of the instant invention showed only a 10% reduction in density, whereas the density of the system where no chelate complex was present was reduced 50%. That is, the system of the instant invention (Sample B) exhibits for superior light fastness to Sample A.

Briefly summarizing the effects achieved by the metal chelate complex employed in the present invention:

(1) The metal chelate complex is readily soluble in organic solvents.
(2) In addition, the structure of the chelate complex can easily be modified so that it permits a large latitude for obtaining desired solubility.
(3) As a result of the latitude of its solubility, the complex is readily enveloped in oil droplets and as a result, photographically undesired interaction with silver halide (e.g., desensitization) is avoidable.
(4) Due to its extremely light solubility, a small amount of the complex is sufficient to effect light fastness; conversely, a large amount can also be employed as in the case of umbrellas, agricultural vinyl cover sheets, etc.
(5) Where the chelate is used a photographic element, no adverse effect on photographic properties is encountered.
(6) The complex is the first fading prevention agent suitable for improving the light fastness of cyan dye images.

For the reasons above, the metal chelate complex used in the instant invention provides excellent light fastness.

What we claim is:

1. A method of improving the light fastness of a photographically useful organic substrate material selected from the group consisting of an anthraquinone dye, a quinoneimine dye, a methine dye, an azo dye, an azomethane dye, a polymethine dye, an indoamine dye, an indophenol dye, a carbonium dye, an indigoid dye, a formazane dye and a fluorescent whitening agent having an absorption peak between about 300 and about 800 nm which comprises making co-exist with said substrate material at least one compound represented by the following general formula (I)

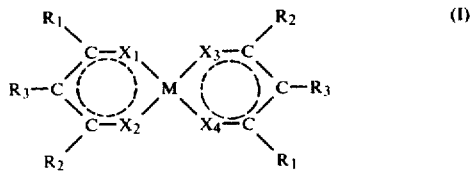

where M represents a metal atom selected from the group consisting of Cu, Co, Ni, Pd and Pt; $X_1$, $X_2$, $X_3$ and $X_4$ each represents an oxygen or sulfur atom; $R_1$ and $R_2$ each represents an alkyl group, an aryl group, a cycloalkyl group, an oxocycloalkyl group or an heterocyclic group which may be substituted or unsubstituted and which may be attached to the carbon atom on the chelate ring directly or through a divalent connecting group; $R_3$ represents a hydrogen atom, an alkyl group, an aryl group, a cycloalkyl group, an oxo-cycloalkyl group or a heterocyclic group which may be substituted or unsubstituted and which may be attached to the carbon atom on the chelate ring directly or through a divalent connecting group; $R_1$, $R_2$ and $R_3$ may be the same or different and $R_1$ and $R_3$, or $R_2$ and $R_3$ may combine to form the non-metallic atoms necessary to complete a 5-, 6- or 7-membered nucleus, said compound of the formula (I) being present in a stabilizing amount which does not adversely affect color hue as well as color purity of the photographically useful organic substrate material.

2. The method of claim 1 wherein said compound represented by general formula (I) is incorporated into a medium containing said organic substrate material.

3. The method of claim 1 where said organic substrate material is a photographic dye image.

4. The method of claim 3 wherein said dye is formed from a dye forming coupler, a DDR coupler, a DRR compound, or a dye developer or is a dye used for a silver dye bleach process.

5. The method of claim 3 wherein said compound is represented by the following general formulae (Ia), (Ib) or (Ic).

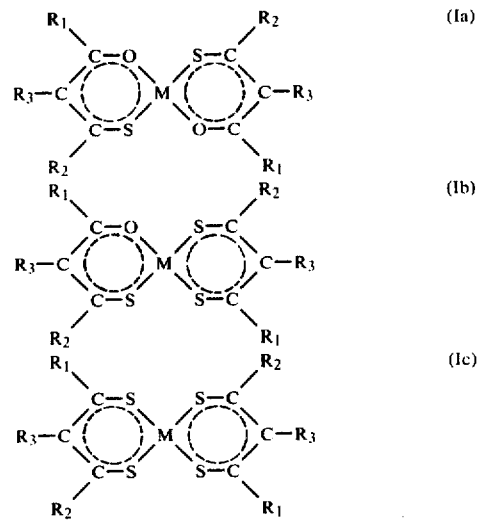

wherein M, $R_1$, $R_2$ and $R_3$ have the same definition as in formula (I).

6. The method of claim 3 wherein said compound is represented by the following general formula (Id) or (Ie):

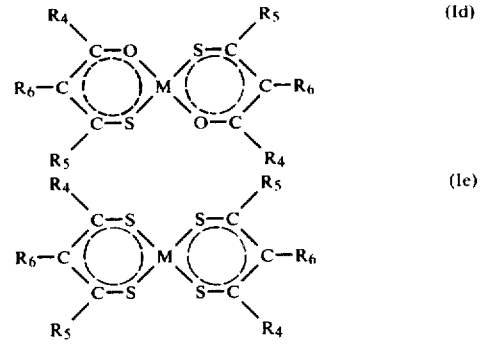

where M represents a metal selected from the group consisting of Cu, Co, Ni, Pd and Pt, $R_4$, $R_5$ and $R_6$ each represents an unsubstituted alkyl group having 1 to 19 carbon atoms, a substituted or unsubstituted alkoxy group having 1 to 19 carbon atoms, a substituted or unsubstituted aryl group, a substituted or unsubstituted aryloxy group, an alkylamino group, an anilino group, a nitrogen-containing heterocyclic group, or a halogen substituted alkyl group, $R_6$ may be hydrogen, and $R_4$, $R_5$ and $R_6$ may be mutually the same or different.

7. The method of claim 4 wherein said dye image is formed by the reaction of a primary aromatic amine color developing agent and a color coupler being a benzoylacetanilide or α-pivalylacetoanilide yellow coupler, a 5-pyrazolone, indazolone, pyrazolinobenzimidazole, pyrazolo-s-triazole or cyanoacetylcoumarone magenta coupler or phenyl or naphthol cyan coupler.

8. A color photographic material comprising at least one layer containing a photographic dye image wherein said layer or an adjacent layer contains a compound of the formula (I) in an amount sufficient to improve the light fastness of said color photographic material

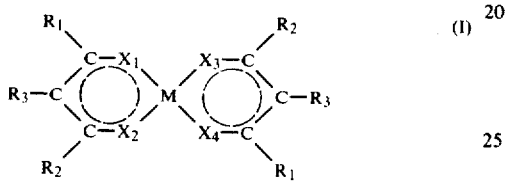
(I)

where M represents a metal atom selected from the group consisting of Cu, Co, Ni, Pd and Pt; $X_1$, $X_2$, $X_3$ and $X_4$ each represents an oxygen or sulfur atom; $R_1$ and $R_2$ each represents an alkyl, an aryl, a cycloalkyl an oxocyclo alkyl, or a heterocyclic group which may be substituted or unsubstituted and which is attached to the carbon atom on the chelate ring directly or through a divalent connecting group; $R_3$ represents a hydrogen atom, an alkyl, an aryl, a cycloalkyl, an oxo-cycloalkyl group or hetercyclic group which may be substituted or unsubstituted and which may be attached to the carbon atom on the chelate ring directly or through a divalent connecting group; $R_1$, $R_2$ and $R_3$ may be the same or different and $R_1$ and $R_3$, or $R_2$ and $R_3$ may combine to form the non-metallic atoms necessary to complete a 5-, 6- or 7-membered nucleus.

9. The color photographic material of claim 8, wherein said photographic dye image is formed from a color coupler, a DDR coupler, a DDR compound, or a dye developer.

10. The photographic element of claim 8, wherein said dye is formed by the reaction of a primary aromatic amine color developing agent and a cyan, magenta, or yellow dye image forming coupler.

11. The photographic material of claim 8 wherein said compound is represented by the general formulae

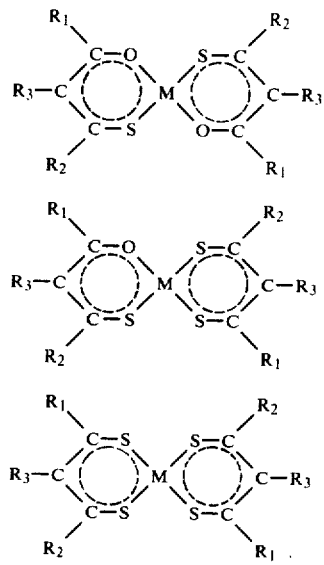

wherein M, $R_1$, $R_2$ and $R_3$ have the same definition as in formula (I).

12. The photographic material of claim 8 wherein said compound is represented by the formulae

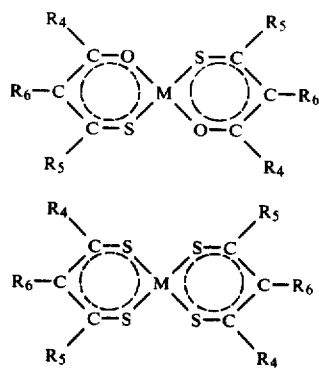

where M represents a metal selected from the group consisting of Cu, Co, Ni, Pd, and Pt., $R_4$, $R_5$ and $R_6$ each represents an unsubstituted alkyl group having 1 to 19 carbon atoms, a substituted or unsubstituted alkoxy group having 1 to 19 carbon atoms, a substituted or unsubstituted aryl group, a substituted or unsubstituted aryloxy group, an alkylamino group, an anilino group, a nitrogen-containing heterocyclic group, or a halogen substituted alkyl group, $R_6$ may be hydrogen, and $R_4$, $R_5$ and $R_6$ may be mutually the same or different.

* * * * *